US00PP30875P2

(12) United States Plant Patent
Hanes

(10) Patent No.: US PP30,875 P2
(45) Date of Patent: Sep. 3, 2019

(54) ***CALIBRACHOA* PLANT NAMED 'CBRZ0022'**

(50) Latin Name: *Calibrachoa hybrida*
Varietal Denomination: CBRZ0022

(71) Applicant: SYNGENTA PARTICIPATIONS AG, Basel (CH)

(72) Inventor: Mitchell E. Hanes, Gilroy, CA (US)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 15/932,956

(22) Filed: May 30, 2018

(51) Int. Cl.
*A01H 5/02* (2018.01)
*A01H 6/82* (2018.01)

(52) U.S. Cl.
USPC ..... Plt./413

(58) Field of Classification Search
USPC ..... Plt./263.1, 413
See application file for complete search history.

*Primary Examiner* — Susan McCormick Ewoldt
*Assistant Examiner* — Karen M Redden
(74) *Attorney, Agent, or Firm* — Dale Skalla

(57) ABSTRACT

A new *Calibrachoa* plant named 'CBRZ0022' particularly distinguished by the mid-sized burgundy flowers with a darker "eye" and yellow inside the flower at the base of the petals, green foliage, good branching, early flowering, and a moderately compact, semi-trailing plant habit, and has little sensitivity to soil pH.

1 Drawing Sheet

Latin name of the genus and species of the plant claimed: *Calibrachoa hybrida.*

Varietal denomination: 'CBRZ0022'.

BACKGROUND OF THE NEW PLANT

The present invention comprises a new *Calibrachoa*, botanically known as *Calibrachoa hybrida*, and hereinafter referred to by the variety name 'CBRZ0022'.

'CBRZ0022' is a product of a planned breeding program. The new cultivar has mid-sized burgundy flowers with a darker "eye" and yellow inside the flower at the base of the petals, green foliage, good branching, early flowering, and a moderately compact, semi-trailing plant habit, and has little sensitivity to soil pH.

'CBRZ0022' originated from a hybridization made in March 2015 in a greenhouse in Gilroy, Calif., USA. The female parent was known as 'CAL4114-5', not patented, a trailing plant with a purple flower. The male parent of 'CBRZ0022' was an unpatented proprietary plant characterized as a compact plant with a rose color flower, known as 'CAL 4103-14', originating from a seedling selected in Gilroy, Calif.

The resulting seeds were sown in August 2015 and 'CBRZ0022' was selected as one flowering plant within the progeny of the stated cross in October 2015 in a controlled environment in Gilroy, Calif.

The first act of asexual reproduction of 'CBRZ0022' was accomplished when vegetative cuttings were propagated from the initial selection in the fall of 2015 in a controlled environment in Gilroy, Calif.

BRIEF SUMMARY OF INVENTION

Horticultural examination of plants grown from cuttings of the plant initiated in the spring of 2016, and continuing thereafter, has demonstrated that the combination of characteristics as herein disclosed for 'CBRZ0022' are firmly fixed and are retained through successive generations of asexual reproduction.

'CBRZ0022' has not been observed under all possible environmental conditions. The phenotype may vary significantly with variations in environment such as temperature, light intensity, and day length.

A Plant Breeder's Right for this cultivar has not yet been applied for. 'CBRZ0022' has not been made publicly available prior to the effective filing date of this application, notwithstanding any disclosure that may have been made less than one year prior to the effective filing date of this application by the inventor or another who obtained 'CBRZ0022' directly from the inventor.

The following traits have been repeatedly observed and are determined to be basic characteristics of the new variety. The combination of these characteristics distinguishes this *Calibrachoa* as a new and distinct variety.

BRIEF DESCRIPTION OF THE PHOTOGRAPHS

The accompanying photographic drawings show typical flower and foliage characteristics of 'CBRZ0022' with colors being as true as possible with an illustration of this type.

Figure 1:
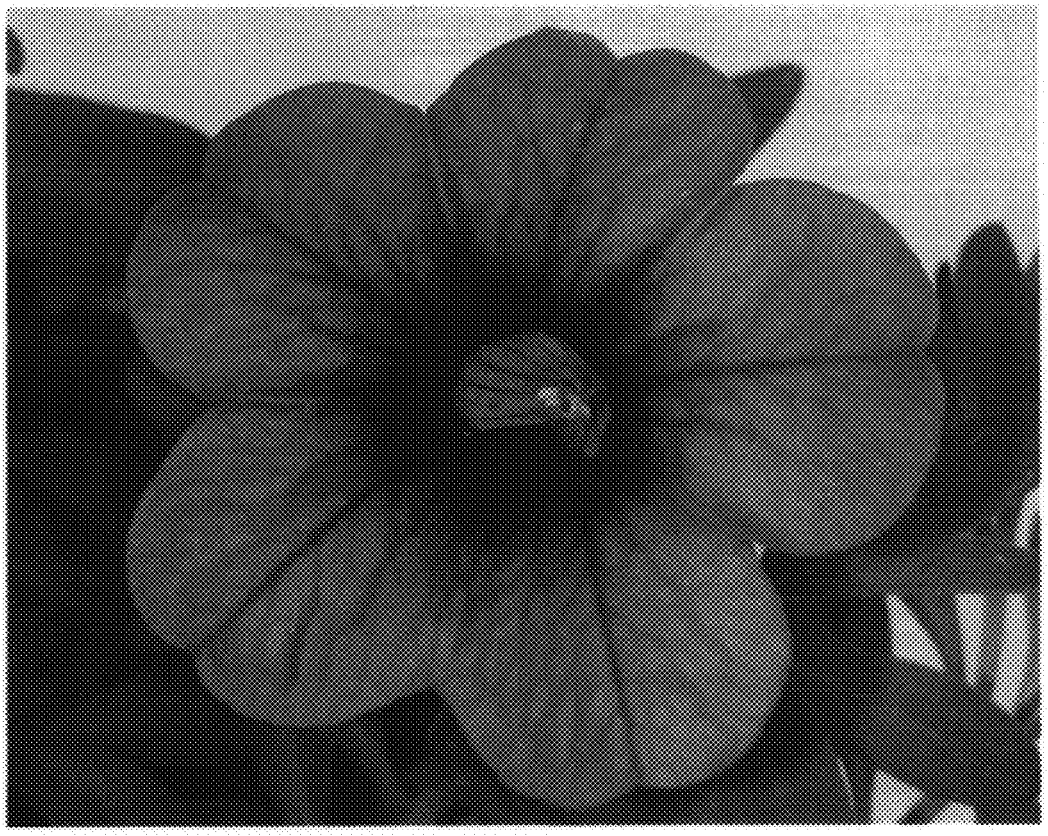
Figure 2:
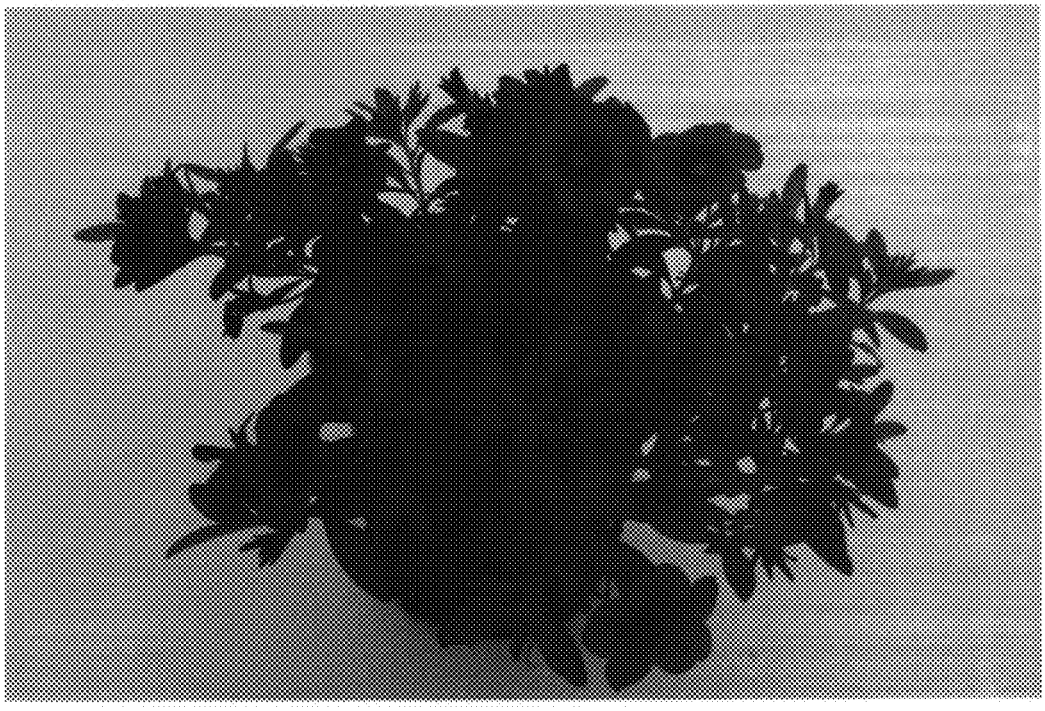

The photographic drawings show in FIG. 1 a close-up of the flowers and in FIG. 2 a flowering plant of the new variety.

DETAILED BOTANICAL DESCRIPTION

The aforementioned photographs were taken in April 2017 in Gilroy, Calif.,

The measurements and observations were made on in Gilroy, Calif. on plants grown in an indoor trial.

Color references are made to The Royal Horticultural Society Colour Chart (R.H.S.) 2015.

TABLE 1

DIFFERENCES BETWEEN THE NEW VARIETY 'CBRZ0022' AND A SIMILAR VARIETY

| | 'CBRZ0022' | 'Callie Burgundy' (PP28071) |
|---|---|---|
| Main flower color: | Burgundy with darker center | Burgundy |
| Earliness to flower: | Early | Later |
| Plant habit as a young plant: | Compact | Trailing |

Plant:

*Form, growth and habit*.—Semi-upright stems, compact and mounding, very well branched.

*Plant height*.—10.0 cm.

*Plant height* (*inflorescence included*).—10-10.5 cm.

*Plant width*.—23-25.0 cm.

*Quantity of main branches*.—5-6.

*Quantity of secondary branches*.—4-6 per basal branch.

*Time to produce a flowering plant*.—7-8 weeks for a 12 cm pot (from planting of rooted cuttings).

Roots:

*Number of days to initiate*.—18 21 days at about 22° C.

*Number of days to produce a rooted cutting*.—21-24 days at 22° C.

*Type*.—Fibrous.

*Color*.—RHS 158D.

Stem:

*Color of stem*.—RHS 144B.

*Length of stem*.—10-14 cm.

*Diameter*.—0.2-0.3 cm.

*Length of internodes*.—0.8-1.5 cm.

*Hairs*.—Present; small.

Foliage:

*Immature leaf, color of upper surface*.—RHS 138A.

*Immature leaf, color of lower surface*.—RHS 138B.

*Mature leaf, color of upper surface*.—RHS 137A.

*Mature leaf, color of lower surface*.—RHS 137C.

*Leaf blade, length*.—3-3.1 cm.

*Leaf, width*.—1.1-1.4 cm.

*Shape*.—Elliptical.

*Base shape*.—Attenuate.

*Apex shape*.—Obtuse.

*Margin*.—Entire.

*Hairs*.—Some present.

*Color of veins, upper surface*.—RHS 138B.

*Color of veins lower surface*.—RHS 138B.

*Petiole color*.—RHS 139C.

*Petiole length*.—0.4-0.5 cm.

*Diameter of petiole*.—0.1-0.15 cm.

*Hairs*.—Present; small.

Inflorescence:

*Type*.—Flowers solitary in upper leaf axis and slanting upright or outwards.

*Quantity of inflorescences per plant*.—20-25.

*Lastingness of individual flowers*.—About 7-9 days.

*Fragrance*.—None.

*Duration of flowering*.—Continuous flowering throughout the summer.

Pedicel:

*Color of pedicel*.—RHS 144B.

*Length of pedicel*.—1.5-1.6 cm.

*Diameter of pedicel*.—1.0 mm.

*Texture of pedicel*.—Hairs.

Flower:

*Immature flowers, corolla upper surface*.—RHS 83A.

*Immature flowers, corolla lower surface*.—RHS 150C with RHS 83A veins.

*Mature flowers, color upper surface*.—RHS 61B with a RHS 1B throat.

*Mature flowers, color lower surface*.—RHS 1B.

*Flower horizontal diameter*.—3.2-3.5 cm.

*Flower height* (*vertical*).—2.5-3.0 cm.

*Corolla tube length*.—1.1 cm.

*Petal apex shape*.—Emarginate.

*Margin*.—Entire.

*Waviness of petals*.—Weak to medium.

*Petal lobation*.—Moderate.

*Corolla texture*.—'Face' papillose and glabrous; rear side with short hair.

*Corolla tube color inside*.—RHS 2C.

*Corolla tube color outside*.—RHS 150C.

Bud (just before opening):

*Color at apex*.—RHS 83A.

*Length*.—2.2-2.5 cm.

*Width* (*upper end*).—0.6-0.8 cm.

*Shape*.—Oblong.

Calyx:

*Number of sepals*.—5.

*Color of sepals, adaxial or upper surface*.—RHS 138A.

*Color of sepals, abaxial or lower surface*.—RHS 138A.

*Length of sepals*.—1.0-1.6 cm.

*Width of sepals*.—0.3-0.4 cm.

*Sepal shape*.—Lanceolate.

*Apex shape*.—Obtuse to acute.

*Margins*.—Entire.

*Texture*.—Small hairs.

Reproductive organs:

*Pistil*.—1.

*Length*.—1.2 cm.

*Style color*.—RHS 145B.

*Style length*.—0.7-0.8 cm.

*Stigma color*.—RHS N144C.

*Number of stamens*.—5.

*Color of filaments*.—RHS 2C.

*Length filaments*.—0.6-1.0 cm.

*Color of pollen*.—RHS 13B.

*Pollen amount*.—Moderate.

*Fertility/seed set*.—Not observed on this hybrid.

*Disease/pest resistance*.—Not observed on this hybrid.

What is claimed is:

1. A new and distinct variety of *Calibrachoa* plant named 'CBRZ0022', substantially as illustrated and described herein.

* * * * *